United States Patent [19]

Mohrman

[11] 4,395,097
[45] Jul. 26, 1983

[54] COMPACT REFRACTION INSTRUMENT
[75] Inventor: Richard C. Mohrman, Rochester, N.Y.
[73] Assignee: Bausch & Lomb Incorporated, Rochester, N.Y.
[21] Appl. No.: 177,144
[22] Filed: Aug. 11, 1980
[51] Int. Cl.³ .............................................. A61B 3/02
[52] U.S. Cl. .................................. 351/201; 351/237; 351/211
[58] Field of Search ..................... 351/5, 7, 13, 26, 27, 351/29, 30, 32, 36, 37, 38, 39

[56] References Cited
U.S. PATENT DOCUMENTS

| | | | |
|---|---|---|---|
| 2,364,793 | 12/1944 | Jobe et al. | 351/36 |
| 3,874,774 | 4/1975 | Humphrey | 351/30 |
| 3,891,311 | 6/1975 | Fletcher et al. | 351/38 |
| 3,927,933 | 12/1975 | Humphrey | 351/39 |

Primary Examiner—R. A. Rosenberger
Attorney, Agent, or Firm—B. D. Bogdon; D. M. Morgan

[57] ABSTRACT

A compact refraction instrument for use in both the objective and subjective examination of human eyes. The instrument incorporates an alignment mode, a retinoscopy mode, a distance mode and near mode. For carrying out the functions associated with these modes, the instrument includes a Brewster stereoscope and a system for supporting a plurality of binocular/monocular vision testing slides. Positioned along the pair of optical paths between the Brewster stereoscope and the slide supporting system are: a first mask/septum system; a mode change system; a second mask/septum system; and a horizontal/vertical target mask system. The instrument also includes a refractor system and apparatus for suspending the refractor system in the optical paths before the Brewster stereoscope. The slide supporting system includes two rotatable concentric drums. The mode change system includes a first mirror for folding the optical paths when the instrument is used for subjective testing at a distance and near vision testing. Alternately, for retinoscopic examination, the paths are folded by a pair of mirrors having an opening therebetween. The Brewster stereoscope and both septums are rotatable so that they can be inserted into or removed from the optical paths as required by the various modes of operation of the instrument.

5 Claims, 19 Drawing Figures

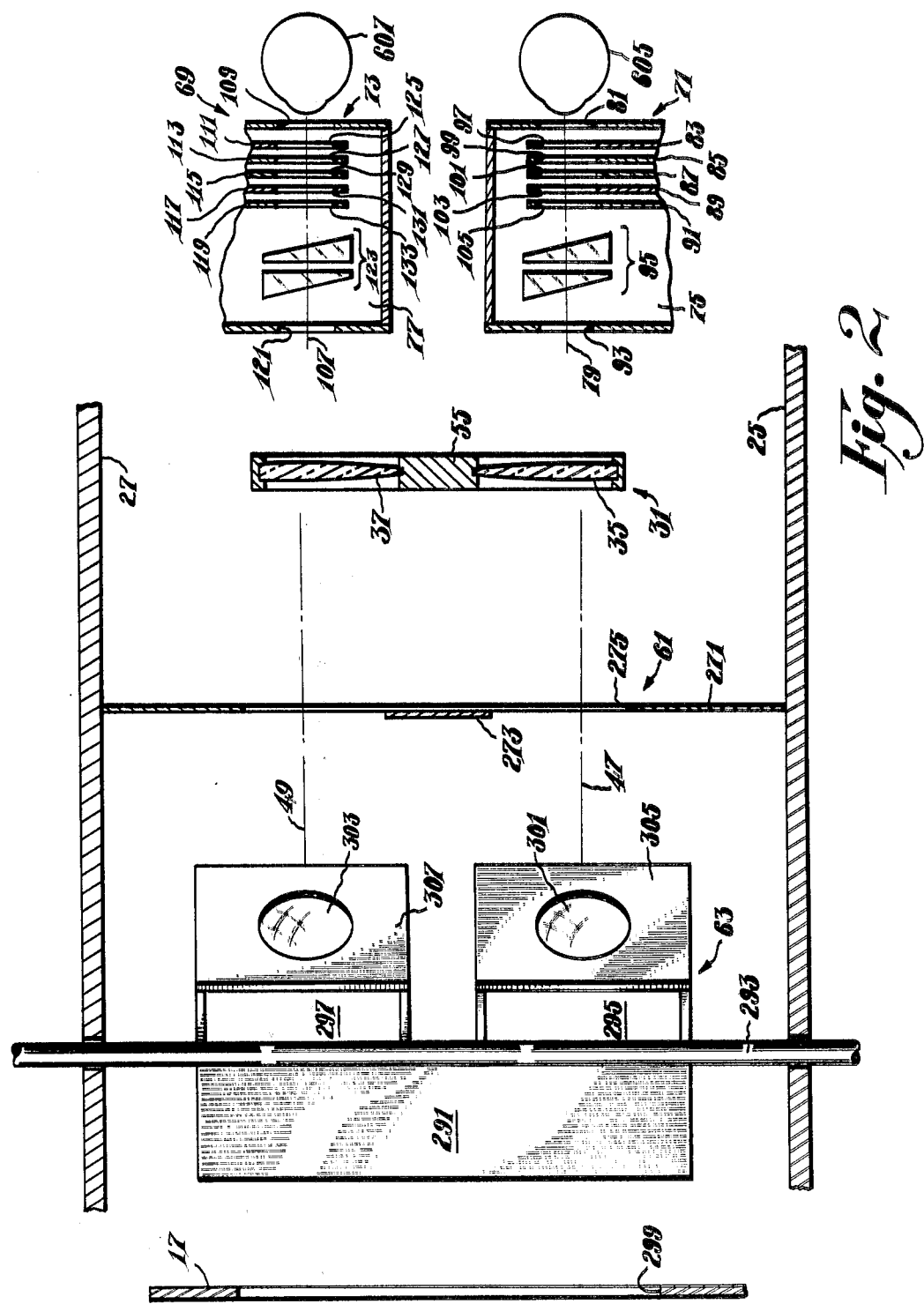

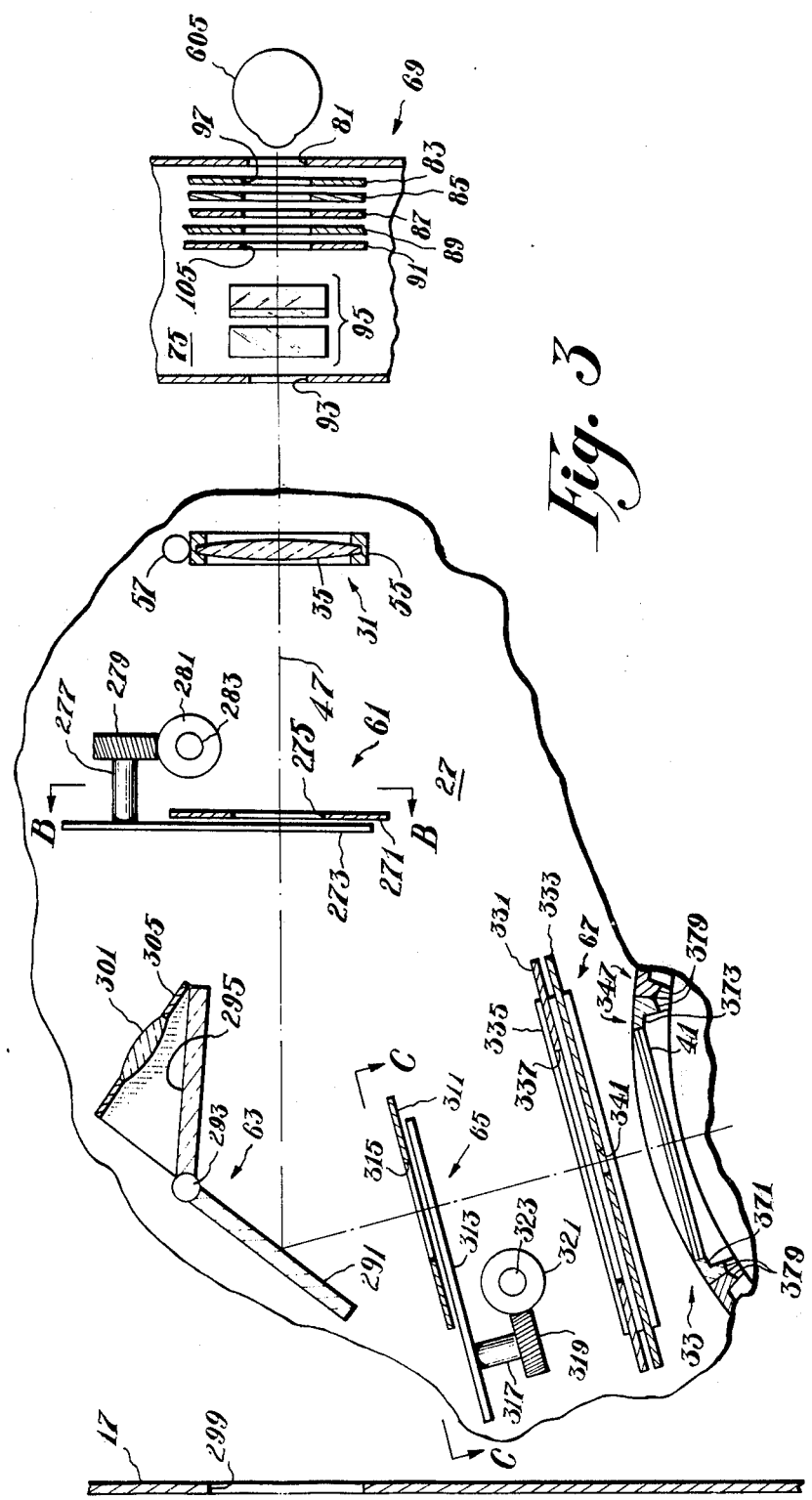

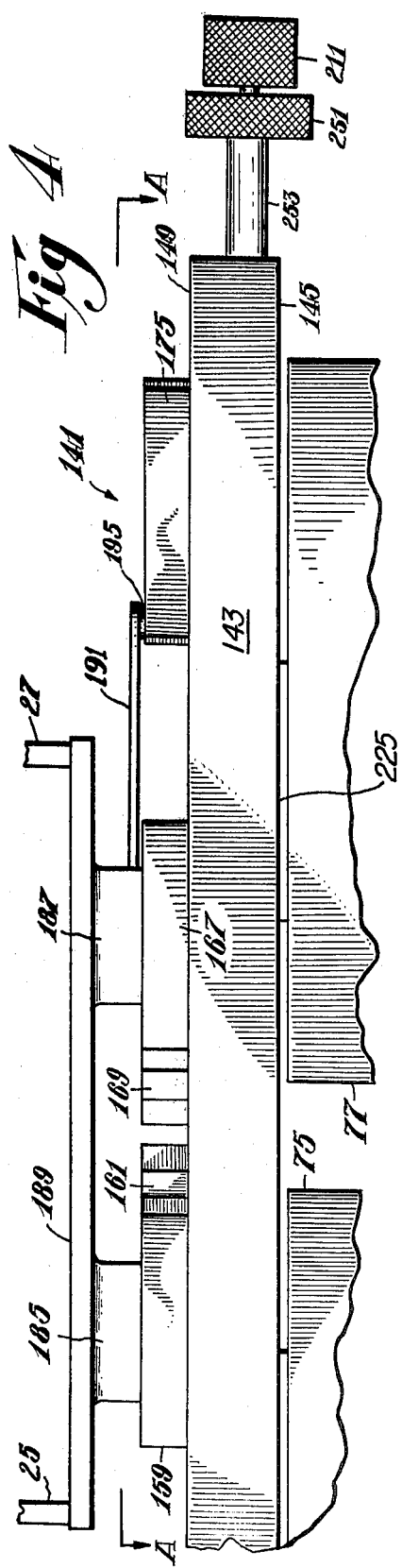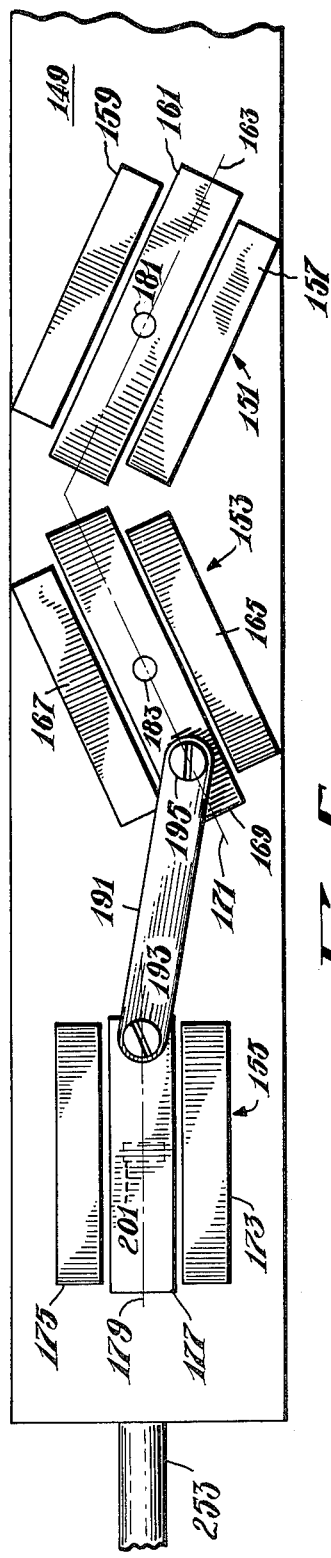

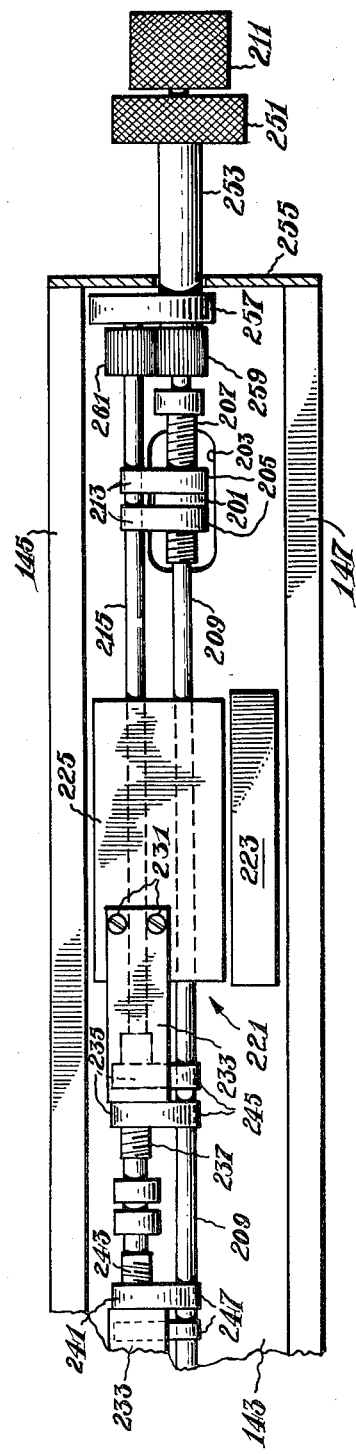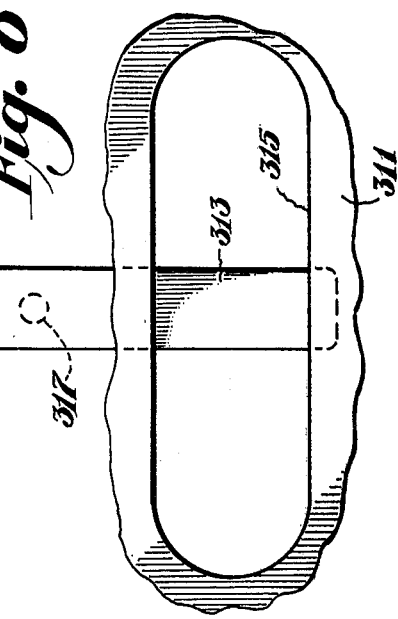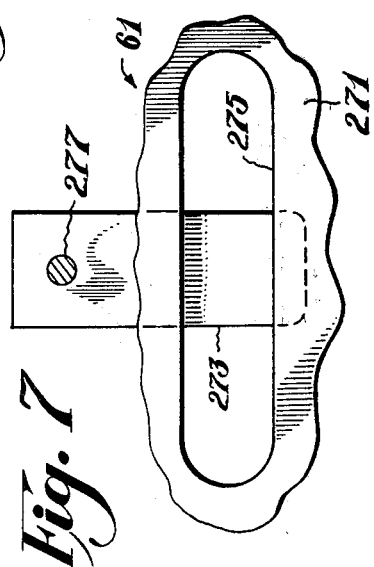

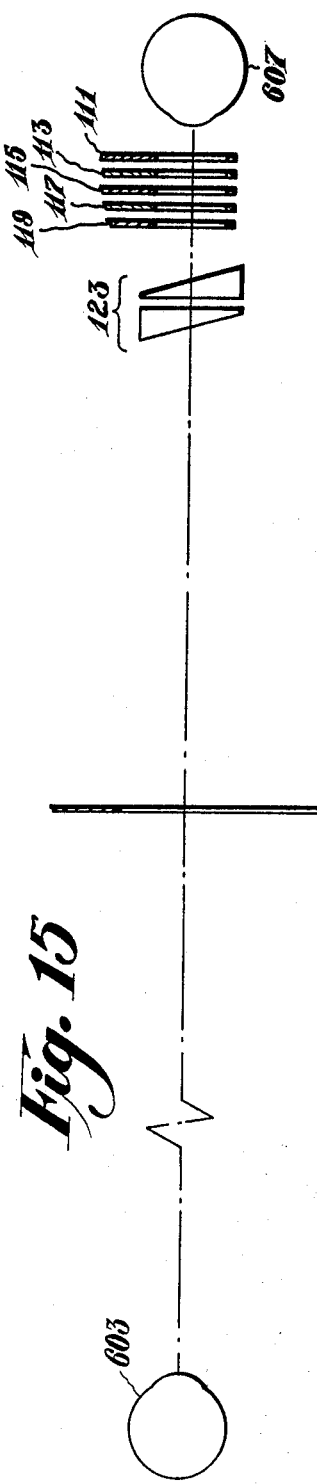
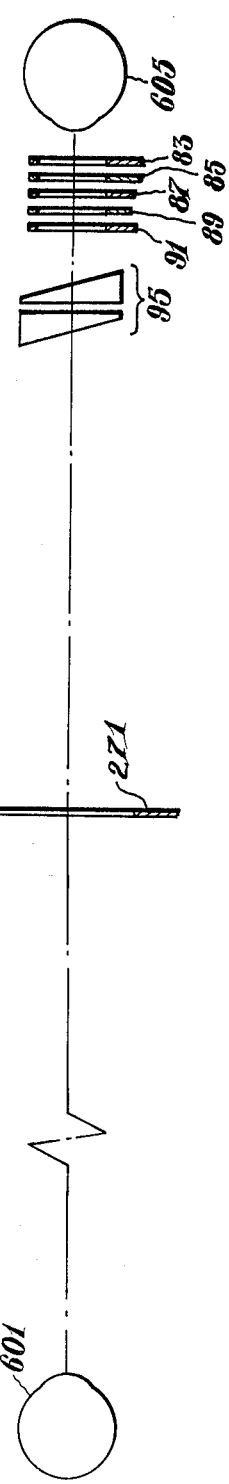
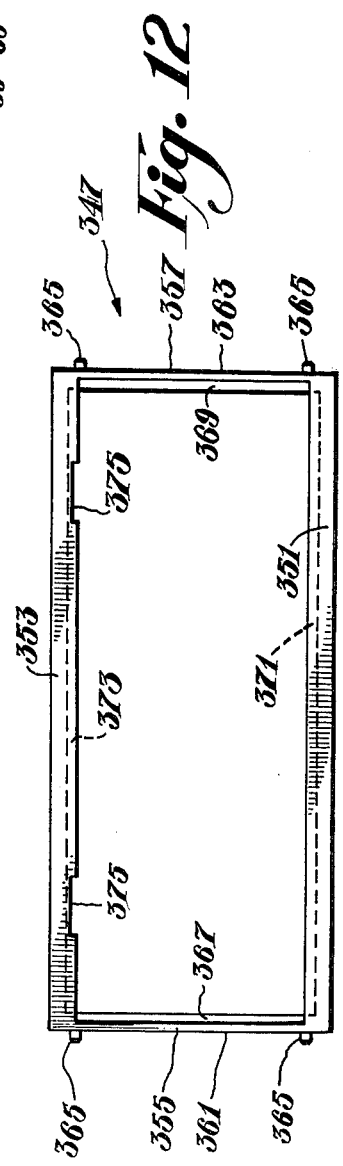
Fig. 15
Fig. 12

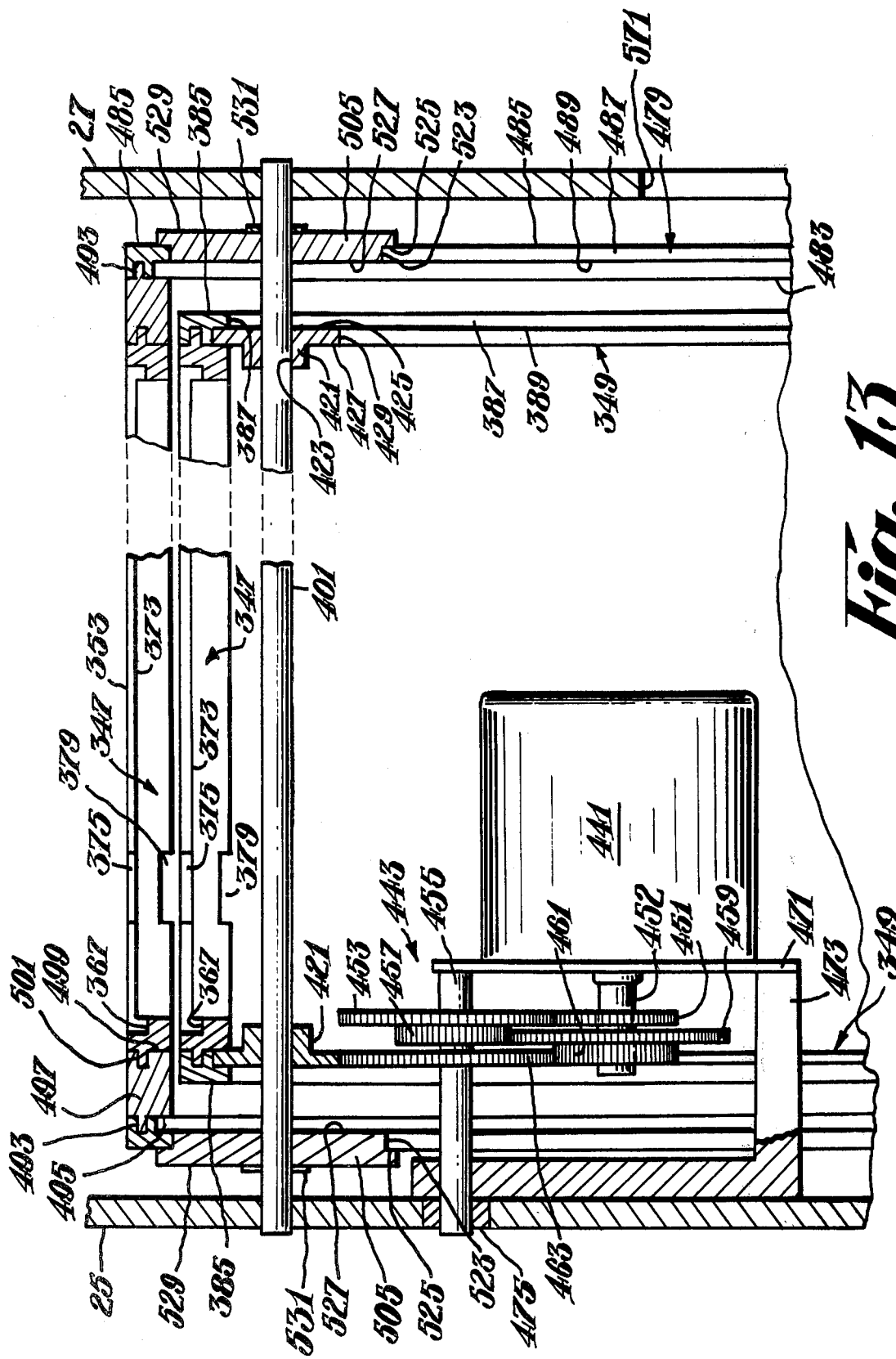

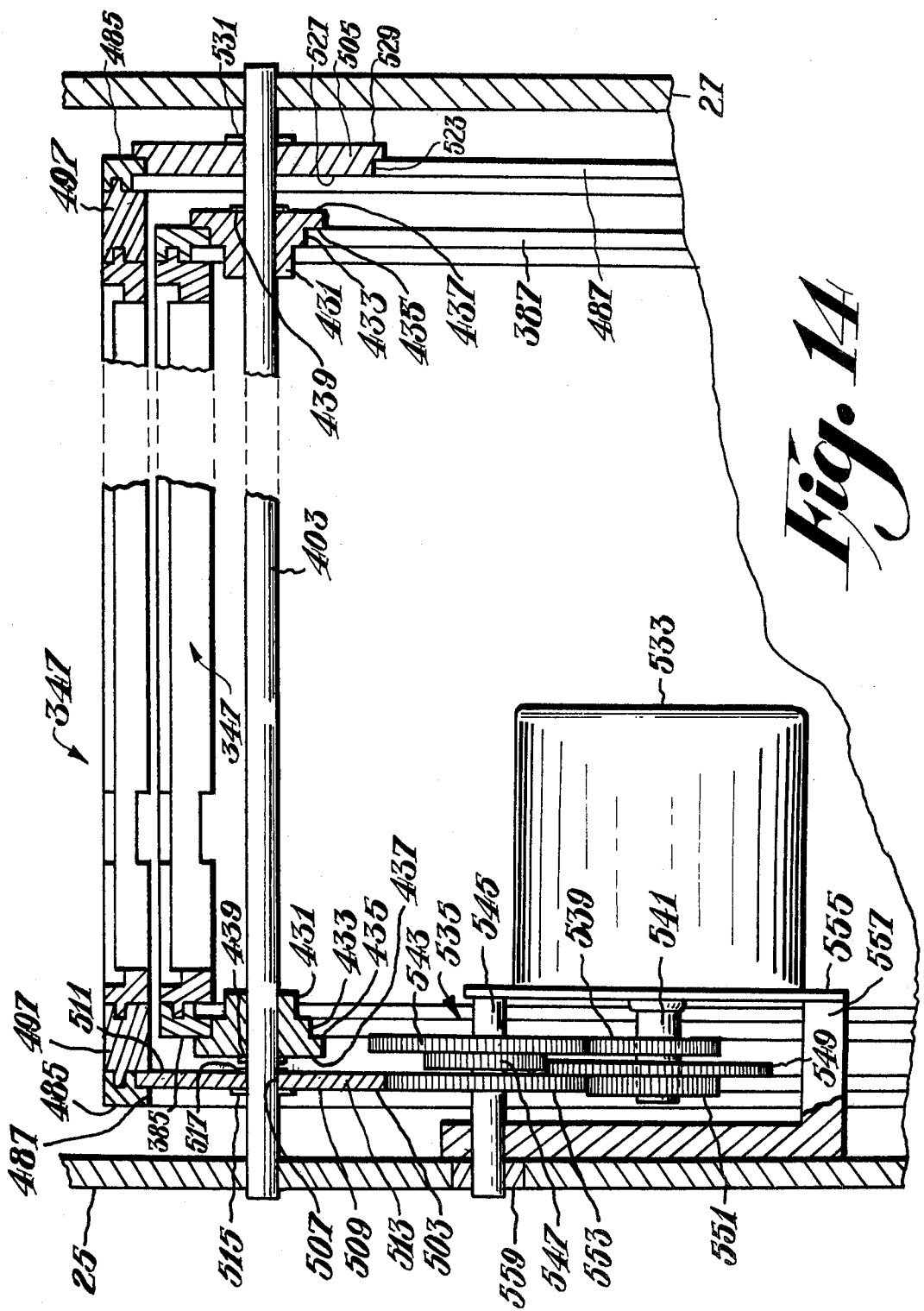

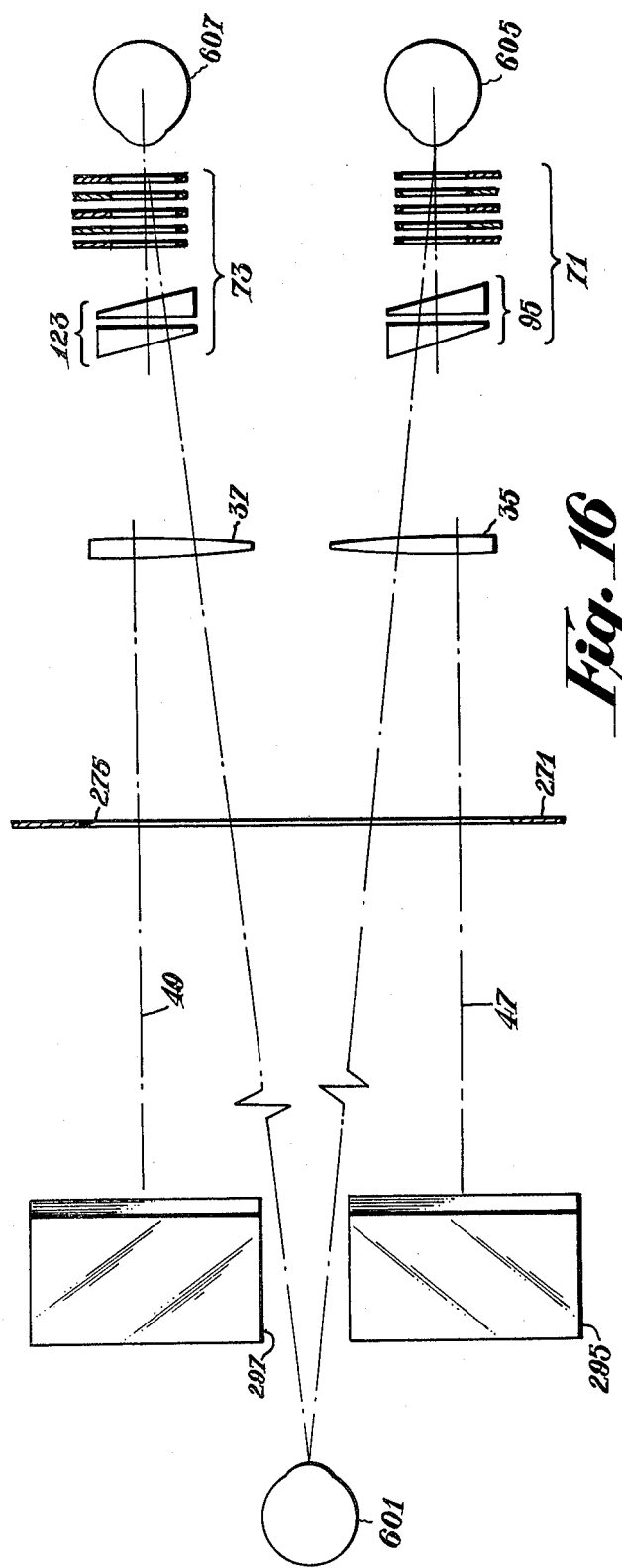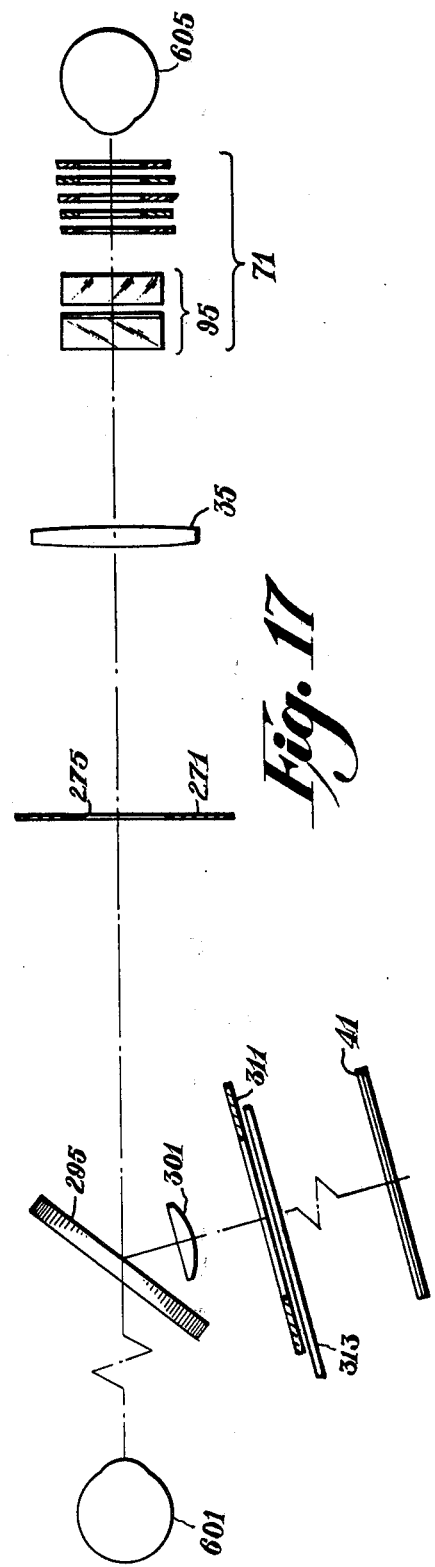
Fig. 16
Fig. 17

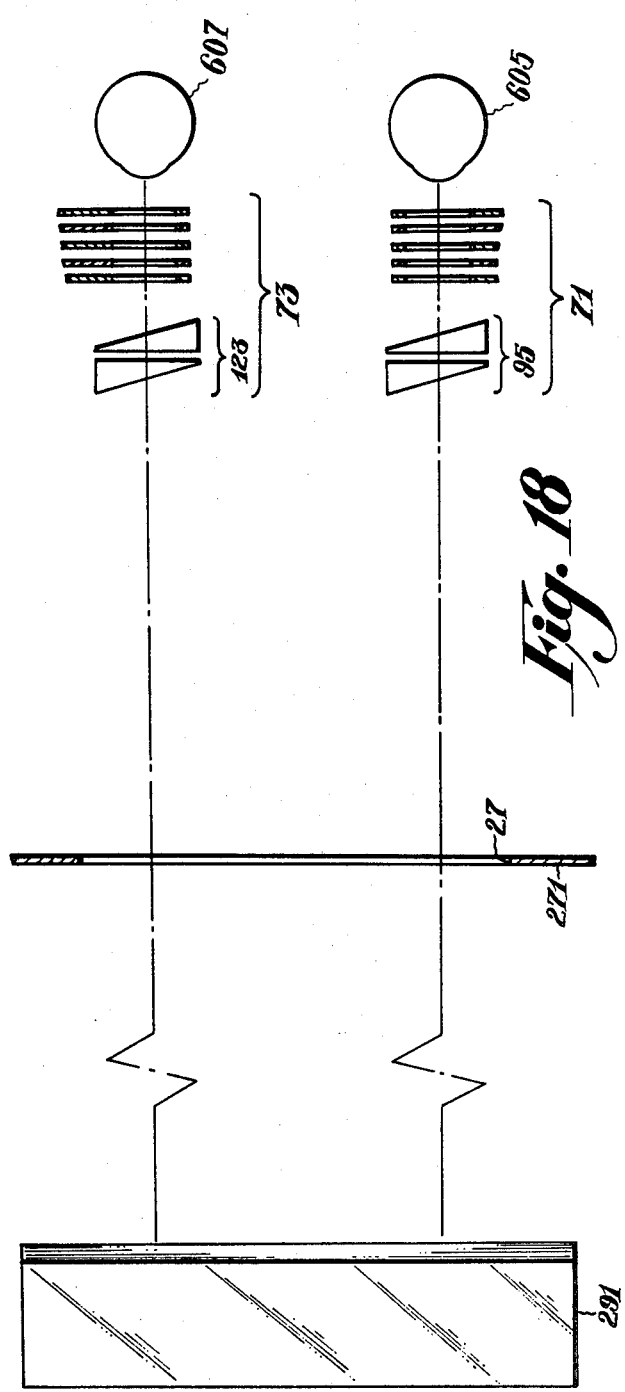
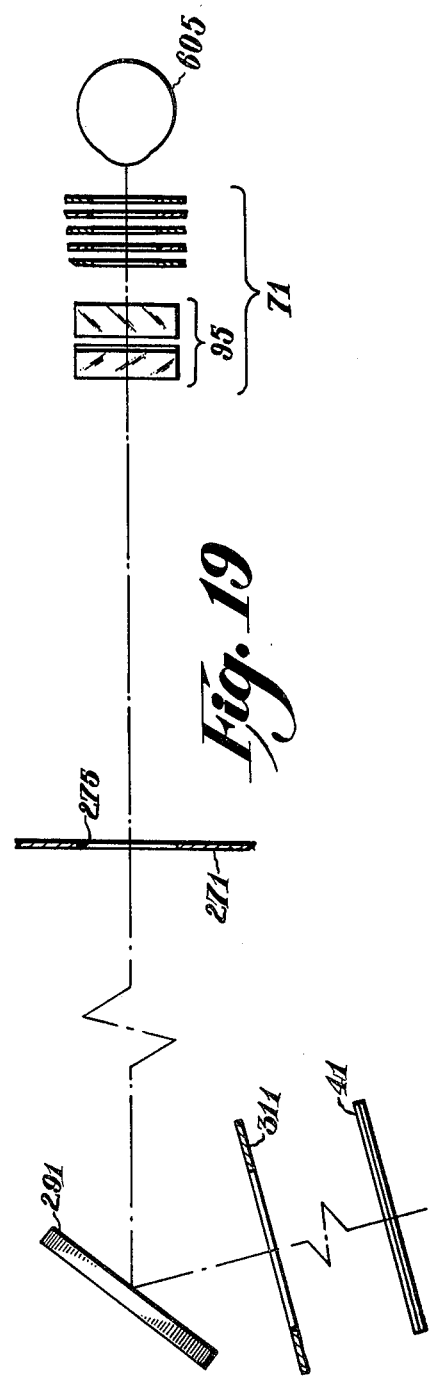

COMPACT REFRACTION INSTRUMENT

CROSS REFERENCE TO RELATED APPLICATIONS

This application is related to the following cofiled applications: Ser. No. 177,143 of P. Augusto et al. for Compact Refraction Instrument; Ser. No. 177,142 of P. Augusto et al. for Compact Refraction Instrument; Ser. No. 177,141 of E. A. Hazard for Concentric Drums Target Support System for Ophthalmic Instrument; and Ser. No. 177,145 of D. E. Stevens for Refractor Suspension System.

DESCRIPTION OF THE PRIOR ART

Ophthalmic instruments are used by ophthalmologists and optometrists to examine eye tissue, determine the optical characteristics of the eye and to test the visual functions. Instruments used to examine eye tissue include ophthalmoscopes, fundus cameras and slit lamps. Instruments used to determine the optical characteristics of the eye include retinoscopes, refractors, optometers, ophthalmometers and keratoscopes. Instruments used for testing visual functions include acuity projectors, refractors, vision testers and visual field testing devices.

A refractor consists of a pair of housings in which are positioned corrective optics for emulating the ophthalmic prescription required to correct the vision of the patient whose eyes are being examined. Typically, each housing contains sets of spherical and cylindrical lenses mounted in rotatable disks. The two housings are suspended from a stand or wall bracket for positioning in front of the patient's eyes. Further, in front of each refractor housing a number of accessories are mounted, typically on arms, so that they may be swung into place before the patient's eyes. A variable power prism known as a Risley prism is one such accessory, as are Maddox rods and Jackson cross cylinders.

In determining a patient's distance prescription, the patient views a variety of alpha numeric characters of different sizes through various combinations of the spherical and/or cylindrical lenses supported in the refractor housings until the correct prescription is emulated. The characters, which are typically positioned 6 meters away, may be on a chart or may be projected on a screen by an acuity projector. For near vision testing the same procedure is repeated, except that the alpha numeric characters viewed by the patient are positioned on a bracket 20 to 65 centimeters in front of the refractor housing.

As those skilled in the art will appreciate, in order to proceed with the subjective determination of a patient's refractive error with a refractor, it is necessary to have a starting point. Typically, this is accomplished by an objective examination of a patient's eyes, through various combinations of the spherical and/or cylindrical lenses supported in the refractor housings, with a retinoscope.

Vision screening instruments for visual classification tests under standarized test conditions are also well known. One such instrument, which is illustrated in U.S. Pat. No. 2,364,739, includes separate drums for supporting far and near vision testing targets, light sources and a pivoted light occluding box adapted for selective alignment with either set of targets. To facilitate fusion of the binocular targets, suitable septums are employed.

U.S. Pat. No. 3,874,774 relates to an eye testing instrument for subjective and objective eye testing. The instrument includes apparatus for projecting a real image of an alpha numeric character, corrective optics and focusing optics. The corrective optics include variable spherical and astigmatic lenses which move relative to one another to emulate the prescription required to correct the vision of the patient whose eyes are being examined. Though not apparent to the patient, the effect of the optical system is the same as if the lenses of the corrective optics were removed from their location in the projector light path and placed immediately in front of the patient's eyes. In operation, once the starting point of the subjective testing is known, a patient looks at the real image projected by the focusing optics. Spherical correction is made by relative movement of the spherical lenses in the corrective optics system. Thereafter, astigmatic input may be made by sequential movement of the variable power astigmatic lenses. The instrument also includes a beam splitter and an additional optical path to permit, inter alia, retinoscopic examination of the patient's eyes. However, in practice, because of the complicated lens systems involved, retinoscopic examinations can not be practically made with this instrument. Thus, to effectively utilize this instrument for subjective examination, it is necessary to determine the starting point with additional apparatus, such as the convential objective examination with a retinoscope and a refractor.

An instrument similar to that described in U.S. Pat. No. 3,874,774 is manufactured by H. Schwind (Germany). It includes a refractor having conventional batteries of spherical and cylindrical lenses, an optical system for projecting a series of vision testing slides and a semi-reflective mirror. In operation the patient whose eyes are to be examined is seated in front of the semi-reflective mirror. A blackboard or other similar surface may be placed on the opposite side to provide a non-distracting background. A target image is projected, via a suitable optics, through various combinations of the spherical and/or cylindrical lenses of the refractor halves for viewing by the patient. Though not apparent to the patient, the optical effect is as though the lenses of the refractor were in front of the patient's eyes. However, the apparatus suffers from the drawback in that there is no way that the examiner can perform a retinoscopic examination on the patient prior to the subjective testing.

U.S. Pat. No. 3,891,311 discloses a compact vision testing apparatus for testing a relatively large number of philosological characteristics of the eye. The head of the patient to be examined is inserted to a viewing port at one end of a light tight housing containing various optical assemblies. Subjective examination of the patient's eyes is accomplished by a refractor assembly carried near the viewing port and a film cassette unit carried within the rear portion of the housing. The latter selectively provides a variety of different visual targets which are viewed through the optical systems of the refractor heads. Again, as with the Schwind instrument and that disclosed in U.S. Pat. No. 3,874,774, a retinoscopic examination cannot be performed and, hence, the starting point of the examination would have to be obtained with additional equipment.

The present invention replaces the refractor/acuity projector combination and the space required by such equipment with a single compact instrument. At the same time, the present invention overcomes the drawbacks of instruments such as disclosed in U.S. Pat. No. 3,874,774 by providing an instrument which permits, with a retinoscope and using conventional techniques, convenient retinoscopic examination of a patient's eyes as well as subjective distance and near vision testing.

SUMMARY OF THE INVENTION

A refraction instrument including apparatus for supporting at least one binocular vision testing target and first and second lenses for making the target appear at or near infinity. The vision testing target and the lenses define a pair of instrument optical paths. The instrument also includes first and second sets of corrective optics for emulating a series of ophthalmic prescriptions, apparatus for separating the optical paths so as to provide separate and independent views of the respective halves of the vision testing target, and apparatus for suppressing accommodation. Finally, the instrument includes apparatus for permitting retinoscopic examination through one of the lenses and one of the sets of corrective optics while simultaneously maintaining a view of at least one of the halves of the vision testing target through at least the other of the lenses and the other of said sets of corrective optics.

BRIEF DESCRIPTION OF THE DRAWINGS

FIG. 2 is a top sectional view of the instrument of FIG. 1 in the distance mode of operation, taken along the optical paths thereof;

FIG. 3 is a side sectional view of the instrument in the distance mode of operation;

FIG. 4 is a top plan view of the refractor mounting system;

FIG. 5 is a back view, taken along line A—A of FIG. 4, of the refractor mounting system;

FIG. 6 is a front view of the refractor mounting system with the refractor housings removed;

FIG. 7 is a sectional view taken along line B—B of FIG. 3;

FIG. 8 is a sectional view taken along line C—C of FIG. 3;

FIG. 12 is a top plan view of one of the mount holders used in the target support system;

FIG. 13 is a sectional view of the target support system taken along line D—D of FIG. 11;

FIG. 14 is an additional sectional view of the target support system taken along line E—E of FIG. 11.

FIG. 15 is a schematic of the instrument in the alignment mode;

FIG. 16 is a top plan schematic of the instrument in the retinoscopy mode;

FIG. 17 is a side schematic of the instrument in the retinoscopy mode;

FIG. 18 is a top plan schematic of the instrument in the near mode of operation; and FIG. 19 is a side schematic of the instrument in the near mode of operation.

DESCRIPTION OF THE PREFERRED EMBODIMENT

Figure 1:
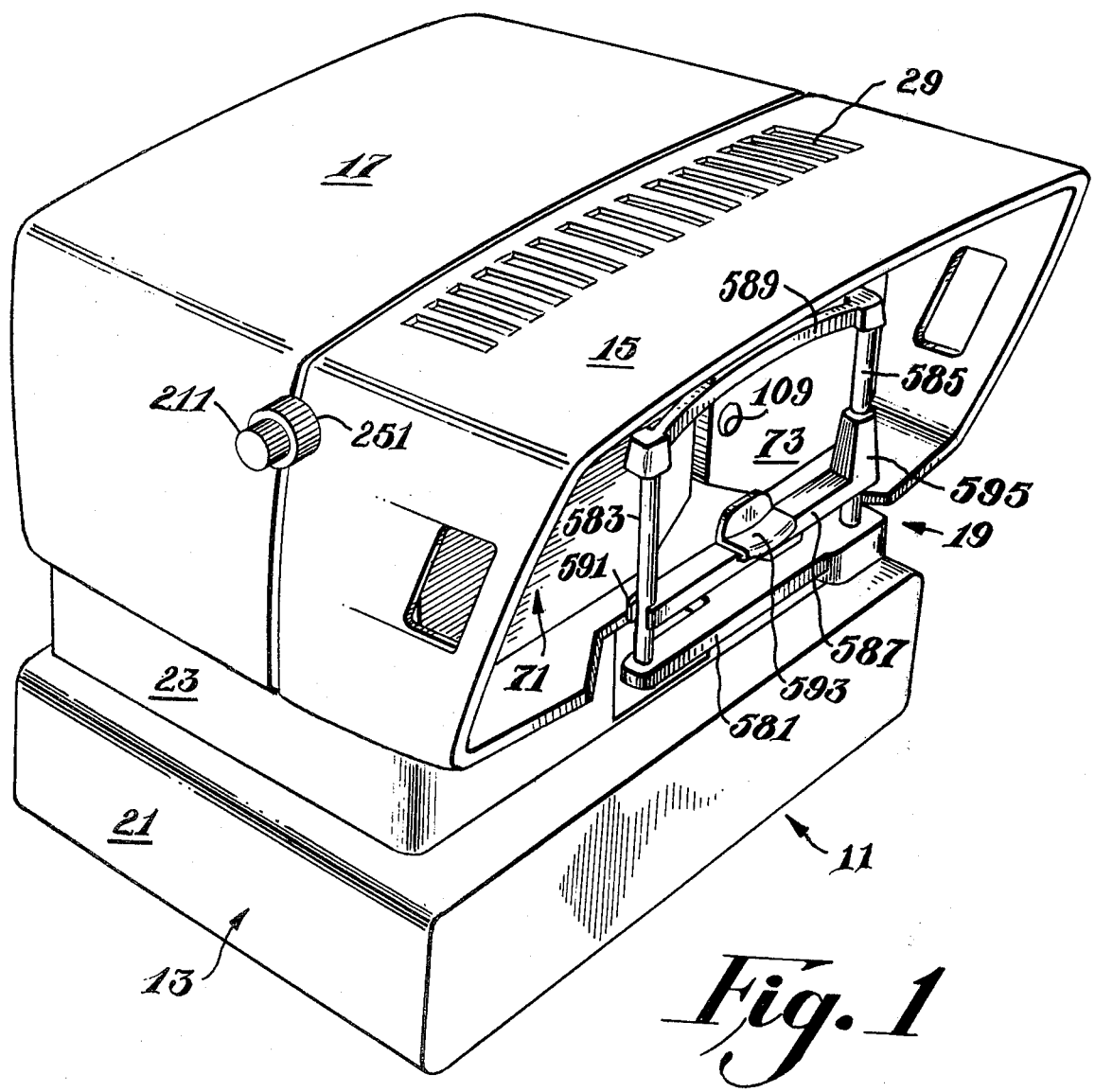
FIG. 1 is a perspective view of the refraction instrument embodying the principles of the present invention.

As illustrated in FIG. 1, instrument 11 includes a base 13, a front housing shroud 15, a rear cover assembly 17 and a head and chin rest assembly 19.

Base 13 includes lower and upper portions 21 and 23 in which are housed various optical, mechanical and electrical components of instrument 11. Base 13 also supports the internal frame of instrument 11 including, as illustrated in FIG. 2, members 25 and 27. In turn, frame members 25 and 27 support rear cover assembly 17 and front housing shroud 15. Shroud 15 includes vents 29.

Figure 11:
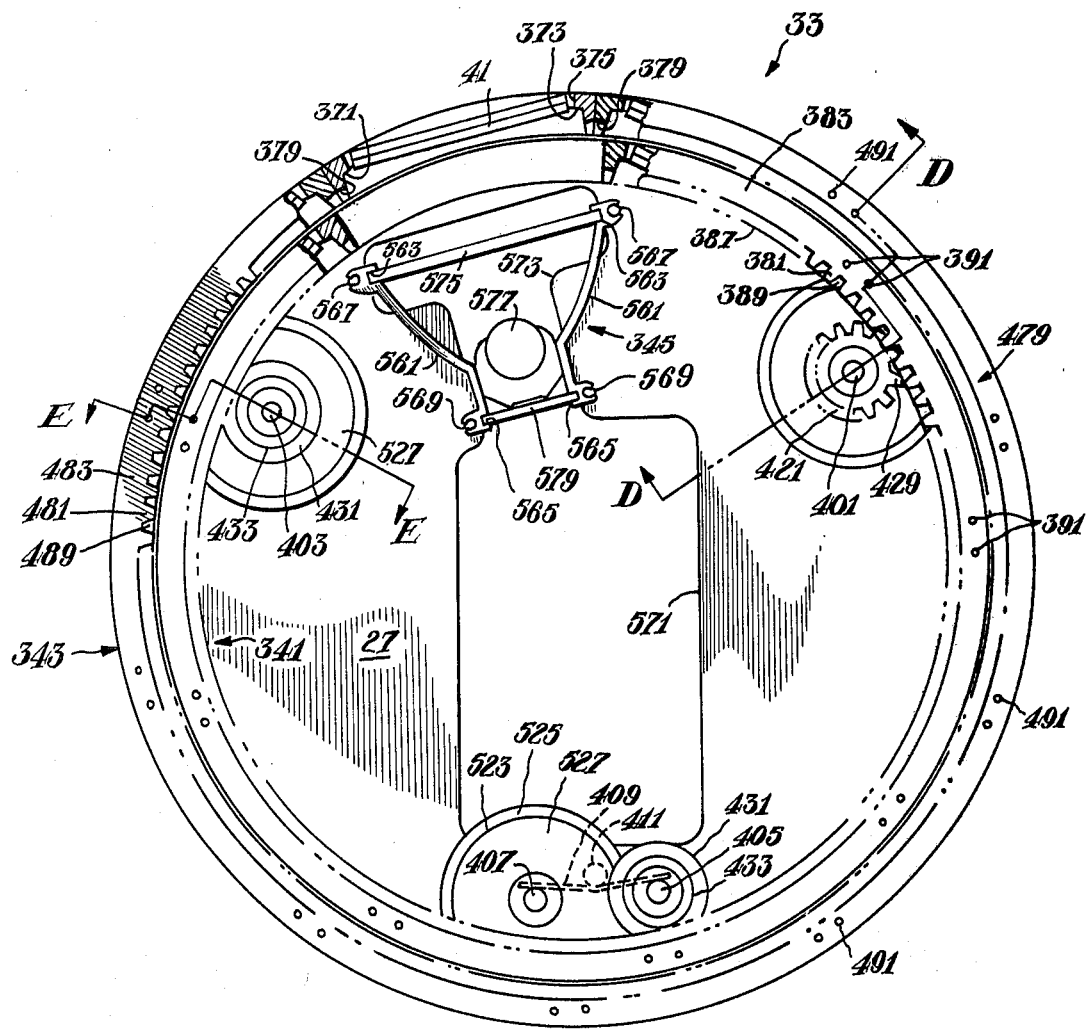
FIG. 11 is an end sectional view of the target support system.

As best illustrated in FIGS. 2, 3 and 11, instrument 11 includes a Brewster stereoscope 31 and a target support system 33. Stereoscope 31 includes first and second decentered lenses 35 and 37 of identical power. Target support system 33 includes a plurality of conventional binocular/monocular vision testing slides, one of which is schematically indicated at 41. In the preferred embodiment of the instrument, such slides are supported on two concentric drums, described hereinafter with reference to FIGS. 11–14. However, as those skilled in the art will appreciate, depending upon the number of slides desired, alternate apparatus such as a single drum or a slide changer may be utilized.

Binocular slides such as indicated at 41 in FIG. 3, typically have identical right and left hand target halves. The center of each of these target halves and the optical axes of lenses 35 and 37 of stereoscope 31, define a pair of instrument optical paths 47 and 49. Supported by frame members 25 and 27, and disposed along paths 47 and 49, between stereoscope 31 and target support system 33, are a first mask/septum system 61, mode change system 63, a second mask/septum system 65, and horizontal/vertical target mask system 67. Positioned in front of stereoscope 31 is apparatus for emulating a series of ophthalmic prescriptions, preferably refractor system 69.

In the preferred embodiment, lenses 35 and 37 have a spherical power of +3.00 D. Since these lenses are decentered, as illustrated in FIG. 2, they provide prismatic power so that a range of interpupilary distances can be accommodated to the fixed distance between the centers of the respective halves of the binocular targets.

For purposes of both retinoscopy and distance vision testing, the lenses 35 and 37 remain in, respectively, optical paths 47 and 49 to make the targets supported on target support system 33 appear at or near infinity. However, when instrument 11 is in the alignment mode, as explained hereinafter, lenses 35 and 37 must be moved out of optical paths 47 and 49. With reference to FIGS. 2 and 3, this is accomplished by supporting lenses 35 and 37 in a frame 55 secured to rotatable shaft 57 which is, in turn, supported either directly or indirectly by frame members 25 and 27. As will be appreciated by those skilled in the art, one or both ends of shaft 57 is connected to further apparatus for rotating the shaft. Such apparatus might include manual knobs. Preferably, however, shaft 57 is motor driven, either directly or indirectly, via a non-slip belt or other positive device drive, with other movable mechanisms housed within instrument 11.

Refractor system 69 includes refractor halves 71 and 73 which contain corrective optics for emulating the ophthalmic prescription for a patient's eye. Like conventional refractor systems such as illustrated in U.S.

Pat. No. 3,860,330, it contains sets of lenses and other conventionally used elements. Typically, each set of lenses is mounted on a rotatable disk so that various lenses can be selectively placed in front of a patient's eye. Further, such components as cylinder lenses are, in addition to being mounted in the rotatable disks, mounted for rotation relative to such disks. In conventional systems such as illustrated in U.S. Pat. No. 3,860,330, positioning of the lenses and other optical elements in front of a patient's eye is accomplished manually. In instrument 11, however, it is preferred to operate various lens supporting discs and other movable components by positively coupling them to motor drives.

With reference to FIGS. 2 and 3, the optics of refractor halves 71 and 73 are mounted in, respectively, housings 75 and 77. In the preferred embodiment housing 75 supports, in order proceeding along refractor optical axis 79 from front opening 81: strong sphere lens disk 83; strong cylinder lens disk 85; weak sphere lens disk 87; weak cylinder lens disk 89; and auxiliary disk 91. Between rear opening 93 and auxiliary disc 91 is a Risley prism assembly schematically indicated at 95. Illustrated aperture 97 in disc 83 is one of a series of apertures for supporting a series of spherical lenses (not shown) ranging, typically, in 4 diopter steps from −28.00 D to +16.00 D. Similarly, aperture 99 is one of a series of apertures in strong cylinder lens disc 85 for supporting a series of strong cylinder lenses (not shown). Depending upon the refraction technique to be used, the cylinder lenses will range, typically, in 2 diopter steps from either −2.00 D to −6.00 D or from +2.00 D to +6.00 D. Aperture 101 is for supporting one of a series of spherical lenses (not shown), range in ¼ diopter steps from 0.00 D to +3.75 D. Similarly, aperture 103 is for supporting one of a series of weak cylindrical lenses (not shown). Again, depending upon the refraction technique to be used, these lenses will range, typically, in ¼ diopter steps from either −0.25 D to −1.75 D or from +0.25 D to +1.75 D. Finally, aperture 105 in auxiliary disk 91, is for supporting one of a series of well known auxiliary elements (also not shown) such as a pinhole, occluder, filters and Maddox rods. For alignment, as discussed hereinafter, one aperture in each of disks 83–91 remains open.

Similarly, mounted within housing 77 of refractor half 73 are, in order proceeding along refractor optical axis 107 from front opening 109: strong sphere lens disk 111; strong cylinder lens disk 113; weak sphere lens disk 115; weak cylinder lens disk 117; and auxiliary disk 119. Supported between rear opening 121 and auxiliary disk 119 is a second set of Risely prisms schematically indicated at 123. Illustrated aperture 125 is one of a series of apertures in strong sphere disk 111 for supporting a series of spherical lenses (not shown) ranging, in 4 diopter steps, from −28.00 D to +16.00 D. Similarly, aperture 127 is one of a series of apertures for supporting a series of strong cylinder lenses (not shown). As with refractor half 71, these cylinder lenses will range, typically, in 2 diopter steps from either −2.00 D to −6.00 D or from +2.00 D to +6.00 D. Aperture 129 is for supporting one of a series of spherical lenses (not shown), ranging in ¼ diopter steps from 0.00 D to +3.75 D. Aperture 131 is for supporting one of a series of weak cylindrical lenses (not shown). Again, depending upon the refraction technique to be used, these lenses will range, typically, in the ¼ diopter steps from either −0.25 D to −1.75 D or from +0.25 D to 1.75 D. Finally, aperture 133 in auxiliary disk 119, is for supporting one of a series of well-known auxiliary elements (also not shown) such as a pinhole, occluder, filters and Maddox rods. For alignment purposes, one aperture in each of disks 111–119 remains open.

As is well known in the art, refractor halves 71 and 74 must be movable relative to each other, in the horizontal direction, to provide for interpupilary distance adjustment. Further, refractor halves 71 and 73 must also be mounted in such a manner as to permit tilt adjustment to compensate for any differences in a patient's eye height. With reference to FIGS. 4, 5 and 6, housings 75 and 77 are attached to frame members 25 and 27 via suspension system 141. Suspension system 141 includes an elongated U-shaped support plate 143, having top and bottom legs 145 and 147 and a back surface 149.

The apparatus for permitting tilt, as best illustrated in FIG. 5, includes three Franke bearing assemblies 151, 153 and 155. Bearing 151 includes blocks 157 and 159 which are secured in any suitable manner (not shown) to surface 149. Slide 161 is supported between blocks 157 and 159 by bearings (not shown) for translation along axis 163. Similarly, bearing 153 includes blocks 165 and 167 secured to surface 149 and slide 169 which translates relative thereto along axis 171. Finally, bearing 155 includes blocks 173 and 175 secured to surface 149 and movable slide 177 which translates along axis 179.

Centered in each of slides 161 and 169 are, respectively, threaded bores 181 and 183. In the no tilt position illustrated in FIG. 5, at the point defined by the intersection of axis 163 and the centerline of bore 181 and the point defined by the intersection of axis 171 and the centerline of bore 183, axes 163 and 171 are tangent to an imaginary circle centered midway between and in the plane of optical axes 79 and 107 of refractor halves 75 and 77. Slides 161 and 169 are pivotally coupled to, respectively, bosses 185 and 187 via pivot screws (not shown) received in bores 181 and 183. Bosses 185 and 187 are, as evident in FIG. 4, part of support plate 189 which, in turn, is connected to frame members 25 and 27 in a suitable manner (also not shown). The apparatus for permitting tilt also includes a link 191 which, via pivot screws 193 and 195, couples slides 169 and 177.

Slide 177 includes a tongue 201 which, as is evident from inspection of FIG. 6, projects through opening 203 provided in support plate 143. The free end of tongue 201 is captured between a pair of nuts 205 which, in turn, are threadedly received on lead screw 207. Lead screw 207 is locked (by means not shown) to shaft 209 for rotation therewith via knobs 211. Rotation of nuts 205 is prevented by providing each with a tab portion 213 which has a U-shaped cut out (not shown) through which passes shaft 215.

In operation, rotation of shaft 209 turns lead screw 207 which, via tongue 201, causes relative motion between slide 177 and both blocks 173 and 175 and support plate 143, to which blocks 173 and 175 are secured. Since slide 177 is coupled to slide 169 via link 191 and since slide 169 can only pivot about its connection with boss 187, the relative motion between slide 177 and support plate 143 results in slide 169 rotating about its mounting with boss 187 while blocks 165 and 167 and support plate 143 move relative to slide 169. The motion of support plate 143 also moves blocks 157 and 159 along axis 163 relative to slide 161, which is pivotally connected to boss 185. In view of the fact that in the centered position axes 163 and 171 are tangent to an imaginary circle centered between axes 79 and 107, the motion of support plate 143 relative to slides 161 and 169 is a rotation about a series of points approximately coincident with the imaginary axis centered between axes 79 and 107. This rotation produces the required tilt of housings 75 and 77.

To move housings 75 and 77 relative to each other, to provide for interpupilary distance adjustment, they are coupled to support plate 143 by a second set of Franke bearing assemblies. With reference to FIGS. 4 and 6, bearing assembly 221 includes a block 223, secured to plate 143, and a slide 225 slidably secured between block 223 and top leg 145 via bearings (not shown) for translation along the longitudinal axis of shaft 215. Secured to slide 255, via screws 231 is an L-shaped bracket 233, the short leg of which is captured between a pair of right hand nuts 235 which are, in turn, threadedly received on right hand lead screw 237. Lead screw 237 is secured to shaft 215 for rotation therewith. In a like manner, the Franke bearing assembly (not shown) which supports refractor housing 75 is also provided with an L-shaped bracket 233, the short leg of which is captured between a pair of left hand nuts 241. Nuts 241 are, in turn, threadedly received on left hand lead screw 243 which is also secured to shaft 215 for rotation therewith. With this arrangement, rotation of shaft 215 rotates lead screws 237 and 243 which, in turn, draw nuts 235 and 241 toward or away from each other, depending upon the direction of rotation of shaft 215. Movement of, for instance, nuts 235 moves, via L-shaped bracket 233, slide 225 and housing 77 which is attached thereto. Rotation of nuts 235 and 241 is prevented by, respectively, integral tabs 245 and 247 which have U-shaped cut outs (not shown) through which pass shaft 209. Rotation of shaft 215 is accomplished via knob 251 mounted on shaft 253 which, in turn, is concentrically mounted on shaft 209. Shaft 253, which passes through an opening in end plate 255, and shaft 215 are supported by bearing block 257 secured to support plate 143. The inner end of shaft 253 supports a gear 259 which meshes with a gear 261 secured to shaft 215.

As is evident from inspection of FIGS. 2, 3 and 7, mask/septum system 61, which is positioned along optical paths 47 and 49 between Brewster stereoscope 31 and mode change system 63, includes a mask 271 secured between frame members 25 and 27 and a movable septum 273. Mask 271, which includes an opening 275, is used to aid in suppression of a patient's accommodation. Septum 273 is positioned between optical paths 47 and 49 when instrument 11 is used in distance vision testing to insure separation of the visual fields of a patient's two eyes. However, when instrument 11 is used in either the alignment, retinoscopy or near vision testing modes, septum 273 must be removed from between optical paths 47 and 49. In the preferred embodiment, septum 273 is rotatable (in the plane of FIG. 7) from the position illustrated in FIG. 7 to a position approximately 90 degrees relative thereto. The apparatus for moving septum 273 includes a rotatable shaft 277 on which is supported a helical gear 279. Helical gear 279 meshes with a second helical gear 281 which, in turn, is secured to drive shaft 283. Drive shaft 283 is rotatably supported between frame members 25 and 27. One or both ends of shaft 283 may be connected to a knob for manual rotation. However, as with Brewster stereoscope 31, it is preferred to drive shaft 283 either directly with a motor or indirectly via a non-slip belt or other positive drive in synchronization with other movable mechanisms housed within instrument 11.

As illustrated in FIGS. 2 and 3, mode change system 63 includes mirror 291, for folding optical paths 47 and 49. Mirror 291 is secured to shaft 293 which, in turn, is rotatably supported between instrument frame members 25 and 27. Also supported on shaft 293 at a suitable angle relative to mirror 291, are a pair of spaced mirrors 295 and 297 which are also used for folding, respectively, optical paths 47 and 49. In the preferred embodiment, the angle between the plane of mirror 291 and the plane of mirrors 295 and 297 is, approximately, 120 degrees.

Mirror 291 is used to fold optical paths 47 and 49 when instrument 11 is used for both subjective testing at a distance and near vision testing. For retinoscopy, as discussed hereinafter, shaft 293 is rotated to the position where mirrors 295 and 297 fold optical paths 47 and 49. In this position (illustrated in FIGS. 16 and 17) the opening between mirrors 295 and 297 is in alignment with window 299 (illustrated in FIGS. 2 and 3) provided in the rear of rear cover assembly 17. Further, fogging lenses 301 and 303, supported on U-shaped brackets 305 and 307, are now positioned on paths 47 and 49 between mode change system 63 and mask/septum system 65. In the alignment mode of instrument 11 (as explained hereinafter in reference to FIG. 15), shaft 293 is rotated to a third position wherein neither optical path 47 nor 49 is folded. Preferably, shaft 293 is driven either directly with a motor, or indirectly via a non-slip belt or other positive drive in synchronization with other movable mechanisms housed within instrument 11.

Mask/septum system 65 includes a mask 311 secured between frame members 25 and 27 and a movable septum 313 as illustrated in FIGS. 3 and 8. Mask 311, which includes opening 315, is used to aid in suppression of a patient's accommodation. Septum 313 is positioned between optical paths 47 and 49 when instrument 11 is used for distance vision testing and retinoscopic examination. However, when instrument 11 is used for near vision testing, septum 313 must be removed from between optical paths 47 and 49. In the alignment mode, the position of septum 313 is immaterial. Septum 313 is rotatable, in the plane of FIG. 8, from the position illustrated in FIG. 8 to a position preferably 90 degrees relative thereto. The apparatus for moving septum 313 includes a rotatable shaft 317 on which is supported a helical gear 319. Helical gear 319 meshes with a second helical gear 321 which, in turn, is secured to drive shaft 323. Drive shaft 323 is rotatably supported between frame members 25 and 27. As will be appreciated by those skilled in the art, the apparatus rotating shaft 323 may be mechanical, electrical, or a combination thereof and may be synchronized as required by the various operating modes of instrument 11 with the movements of mode change system 63, mask/septum system 61 and Brewster stereoscope 31.

Figure 9:
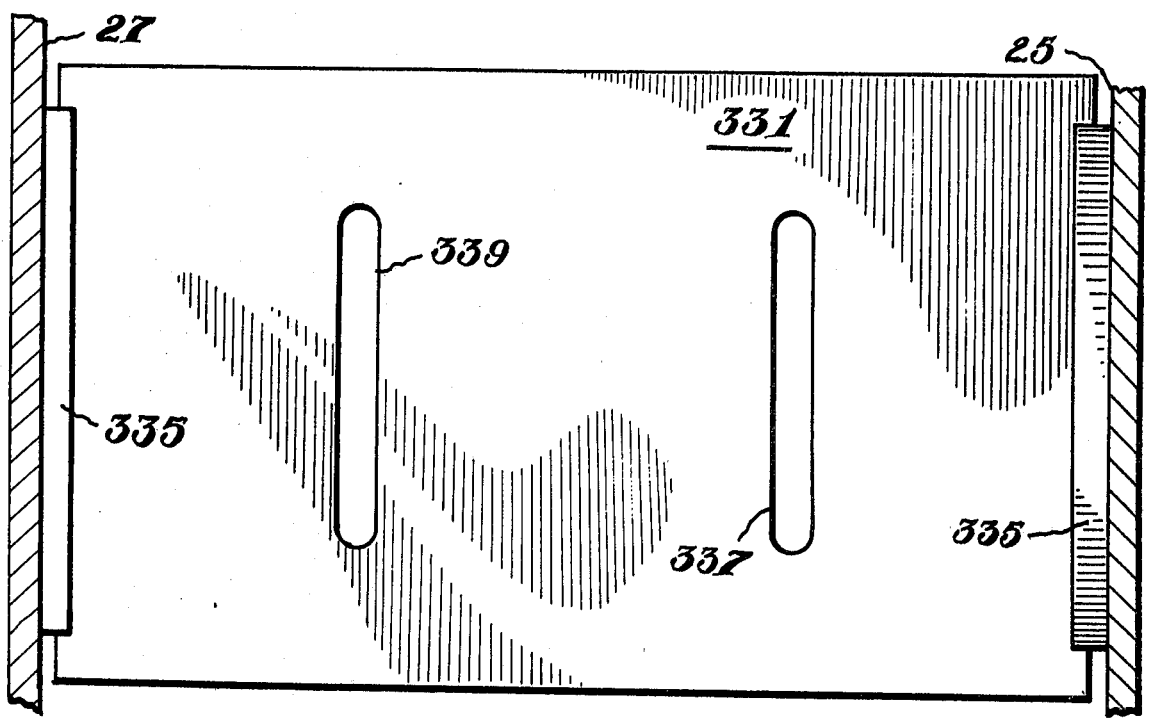
FIG. 9 is a top plan view of the vertical target mask.
Figure 10:
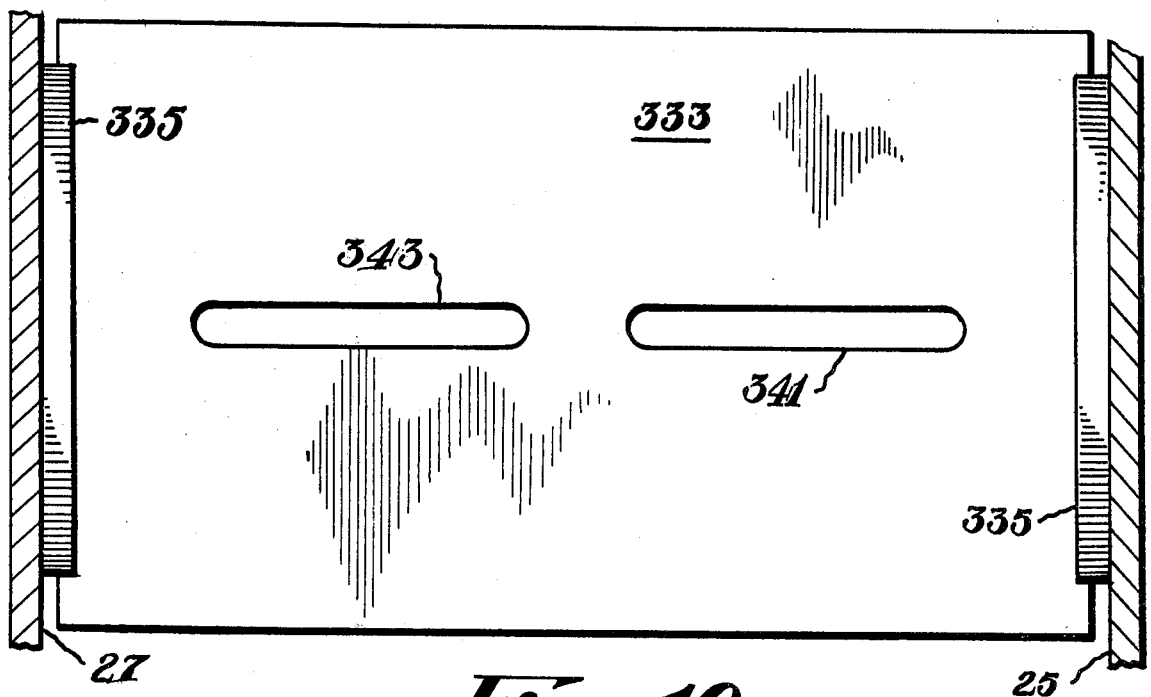
FIG. 10 is a top plan view of the horizontal target mask.

Horizontal/vertical target mask system 67, interposed between mask/septum 65 and target support system 33, includes vertical mask 331 and horizontal mask 333. As illustrated in FIGS. 3, 9 and 10, masks 331 and 333 are supported between frame members 25 and 27 by guides 335. Mask 331 includes a pair of vertical slits 337 and 339, for masking all but certain vertical areas from a patient's field of view. Similarly, mask 33 has a pair of horizontal slits 341 and 343 for masking all but certain horizontal areas from a patient's field of view. When used together, as illustrated in FIG. 3, slits 337, 339 and 341, 343 mask all but a pair of spots from a patient's field of view. Movement of masks 331 and 333 is preferably controlled by motors (not shown) through a suitable drive mechanism such as a cable and pulley system or, alternately, a rack and pinion mechanism.

Binocular target assembly 33 includes an inner drum 341, an outer drum 343 and a light source assembly 345. Inner drum 341 is formed from eight mount holders 347 supported between a pair of ring gear members 349. Though there is space for a ninth mount holder, it is omitted to prevent inadvertent placing of a vision testing slide between the light source assembly 345 and a slide supported on the outer drum 343 in alignment with light source assembly 345, as illustrated in FIG. 11.

As shown in FIGS. 11-14, each mount holder 347 is in the form of a rectangular frame and includes side portions 351 and 353 and end portions 355 and 357. End portions 355 and 357 include mounting surfaces 361 and 363 and integral mounting pins 365. End portions 355 and 357 also include, respectively, recessed support shoulders 367 and 369. Side portion 351 has a lip 371, while side portion 353 has a lip 373 and a pair of cut outs 375. Finally, noting FIGS. 13 and 14, side portions 351 and 353 have clearance cut outs 379. Preferably, holders 347 are of molded plastic such as polycarbonate material.

Various testing slides, such as schematically indicated at 41 in FIG. 3, which are received in each of the mount holders 347, preferably take the form of a photographic positive with the required target or targets thereon sandwiched between two pieces of glass. These sandwiches are received in a plastic frame (not shown) which includes a lip which cooperates with lip 371, ends which cooperate with shoulders 367 and 369 and a pair of spring elements adapted to be received in recesses 375. The spring elements themselves include lips which cooperate with lip 373 to hold each slide in its respective holder 347.

Ring gear members 349 are, preferably, of molded plastic such as polycarbonate material. As illustrated in FIGS. 11, 13 and 14, each member 349 includes: 126 internal spur gear teeth 381; inner mounting surface 383; outer surface 385; shoulder 387; and flange surface 389. Inner mounting surface 383 is, as best illustrated in FIG. 11, provided with a plurality of uniformly spaced bores 391 which receive pins 365 on mount holders 347 to form inner drum 341. As illustrated in FIG. 13, with pins 365 received in bores 391, surfaces 361 and 363 are held in engagement with mounting surfaces 383 in any convenient manner, such as by adhesive.

The manner of supporting drum assemblies 341 and 343 between frame members 25 and 27 is best illustrated in FIGS. 11, 13 and 14. The support system includes shafts 401, 403, 405 and 407. Shafts 401 and 403 are common to both support systems, while shaft 405 is only used in retaining inner drum assembly 341 and shaft 407 is only used in retaining outer drum assembly 343. Shafts 401 and 403 are supported, by bearings (not shown) in frame members 25 and 27, for rotational movement about their respective longitudinal axes. Shafts 405 and 407 are each received in a pair of elongated slots (not shown) provided in frame members 25 and 27 and biased radially outward from the axis of rotation of drum assemblies 341 and 343 by a pair of leaf springs such as shown at 409. As illustrated in FIG. 11, spring 409 is held in position by pin 411 received in frame member 27.

As best illustrated in FIGS. 11 and 13, inner drum 341 is supported by a pair of gears 421, each having bore 423 which receives shaft 401. Gears 421 also include outer face 425, inner face 427 and gear teeth 429 which, in the assembled instrument mesh with gear teeth 381 in ring gear members 349. Gears 421 are keyed to shaft 401 to prevent relative rotational movement. Further, movement of gears 421 along shaft 401 is prevented as inner and outer faces 427 and 425 are captured between flange surfaces 389 of ring gear members 349 and portions of mounting surfaces 361 and 363 of mount holders 347. Gears 421 could also be cemented to shaft 401.

With reference to FIGS. 11 and 14, rotatably supported on each of shafts 403 and 405 are pairs of rollers 431, each of which has a surface 433 adapted for engagement with shoulder 387 or ring gear members 349. Rollers 431 also include an inside face 435 and an outside face 437. Movement of roller 431 along shafts 403 is prevented by capturing faces 435 and 437 between face 385 of ring gear member 349 and lock rings 439. Lateral movement along shaft 405 is also prevented by lock rings (not shown). The radially outward force exerted on shaft 405 via springs 409 simultaneously urges teeth 429 into engagement with teeth 381 and surfaces 433 on rollers 431 into engagement with shoulders 387, to center inner drum 341 about its axis of rotation. In theory, shaft 405 could be fixed instead of supported in slots. However, by permitting shaft 405 to float in the radial direction, binding of drum 341 during rotation, which might result from manufacturing tolerances, is avoided. This arrangement also helps to reduce noise and vibration.

As illustrated in FIG. 13, one of gears 421 is driven by stepping motor 441 via gear system 443. Gear system 443 includes: first gear 451 secured to shaft 452 of motor 441; second gear 453 rotatable about shaft 455; third gear 457 secured to gear 453; fourth gear 459 rotatably supported on shaft 452; fifth gear 461 secured to gear 459 for rotation therewith; and sixth gear 463, also rotatably supported on shaft 455. Gear 463 meshes with gear 421 to, in turn, drive drum 341. Movement of gears 453, 457 and 463 along shaft 455 is prevented by lock rings (not shown). Preferably, gear 451 has 14 teeth; gear 453, 28; gear 457, 14; gear 459, 28; gear 461, 14; gear 463, 28; and gear 421, 14. With this arrangement, an 8 to 1 reduction between the rotation of shaft 452 of motor 441 and rotation of gears 421 is obtained.

Motor 441 is supported on plate 471 which is secured to L-shaped bracket 473. Shaft 455 is supported by plate 471 and bracket 473. Further, as illustrated in FIG. 13, shaft 455 is also received in eccentric bushing 475 in frame member 25 to thereby support motor 441 and gear system 443. Rotation of bushing 475 adjusts the mesh between gear 463 and gear 421.

Outer drum 343 is formed from nine mount holders 347, such as illustrated in FIGS. 11, 12, 13 and 14, supported between a pair of ring gear members 479. Though there is space for a tenth mount holder, it is omitted to prevent the inadvertent placing of a vision testing slide between horizontal/vertical target mask system 67 and a slide supported on inner drum 341 and in alignment with light source assembly 345 for viewing.

Ring gear members 479 are, preferably, of molded plastic, such as polycarbonate material. As illustrated in FIGS. 11, 13 and 14, each member 479 includes: 140 internal spur gear teeth 481; inner mounting surface 483; outer surface 485; shoulder 487; and flange surface 489.

Inner mounting surface 483 is, as best illustrated in FIG. 11, provided with a plurality of uniformly spaced bores 491 which receive pins 493 on surface 495 of spacer blocks 497. Spacer blocks 497 also include a second mounting surface 499 having bores 501. As illustrated in FIGS. 13 and 14, with pins 365 received in bores 501 and pins 493 received in bores 491, surfaces 361 and 363 are held in engagement with mounting surfaces 499 (by, for instance, adhesive) and surfaces 495 are held in engagement with mounting surfaces 483 (also by, for instance, adhesive) to form outer drum 343.

With reference to FIGS. 11, 13 and 14, outer drum 343 is supported by: (1) a gear 503 and roller 505 on shaft 403; and (2) pairs of rollers 505 on shafts 401 and 407. Gear 503 has a bore 507 which receives shaft 403. Gear 503 also includes outer face 509, inner face 511 and gear teeth 513 which, in the assembled instrument, mesh with gear teeth 481. Lateral movement of gear 503 along shaft 403 is prevented by lock washers 515 and 517.

Each of the rollers 505, rotatably supported on shafts 401, 403 and 407 has a surface 523 adapted for engagement with shoulder 487 of ring gear members 479. Each roller 505 also includes a lip 525, inside face 527 and an outside face 529. Movement of rollers 505 along shaft 401 is prevented because lips 525 are held in engagement with outer surface 485 of ring gear members 479 by lock rings 531. Lateral movement along shaft 407 is prevented by lock rings (not shown). The radially outward force exerted on shaft 407 via springs 409 simultaneously urges teeth 513 into engagement with teeth 481 and surfaces 523 on rollers 505 into engagement with shoulders 487. This centers out drum 343 about its axis of rotation, which is coincident with the axis of rotation of inner drum 341. As with shaft 405, shaft 407 is permitted to float in the radial direction, to prevent binding and reduce noise and vibration.

As illustrated in FIG. 14, gear 503 is driven by stepping motor 533 via gear system 535. Gear system 535 includes: first gear 539 secured to shaft 541 of motor 533; second gear 543 rotatable about shaft 545; third gear 547 secured to gear 543; fourth gear 549 rotatably supported on the shaft of motor 533; fifth gear 551 secured to gear 549 for rotation therewith; and sixth gear 553, also rotatably supported on shaft 545. Gear 553 meshes with gear 503 to, in turn, drive outer drum 343. Movement of gears 543, 547 and 553 along shaft 545 is prevented by lock rings (not shown). Preferably, gear 539 has 14 teeth; gear 543, 28; gear 547, 14; gear 549, 28; gear 551, 14; gear 553, 28; and gear 503, 28. With this arrangement, an 8 to 1 reduction between the rotation of shaft 541 of motor 533 and rotation of gear 503 is also obtained. Thus, for identical angular rotations of, respectively, shafts 452 and 541 of motors 441 and 533, gears 421 and 503 undergo equal angular rotations. With this arrangement, and with the gear ratios of 126:14 (between gears 421 and 349) and 140:28 (between gears 503 and 479), the angular rotation of motor shaft 452 required to move a vision testing slide (supported on inner drum 341) from a position in alignment with optical paths 47 and 49 to a position in which an immediately adjacent vision testing slide in aligned with optical paths 47 and 49, is the same as that rotation required of motor shaft 541 to displace a vision testing slide (supported on outer drum 343) an equal distance.

Motor 533 is supported on plate 555 which is attached to L-shaped bracket 557. Shaft 545 is supported by plate 555 and bracket 557. Further, as illustrated in FIG. 14, shaft 545 is also recrived in eccentric bushing 559 in frame member 25 to thereby support motor 533 and gear system 535. Rotation of bushing 559 adjusts the mesh between gear 553 and 503.

As best illustrated in FIG. 11, light source assembly 345 includes a pair of brackets 561 each having a first slot 563, a second slot 565 and a pair of arcuate slots 567 and 569. Each bracket 561 is of a length equal to the distance between frame members 25 and 27. Brackets 561 are assembled in place by inserting them either through opening 571 or 573 in support plate 27 and holding them in place by screws (not shown) which pass through the support plates and tap into arcuate slots 567 and 569. With brackets 561 in place, translucent diffusing screen 575 is received in slots 563 and fluorescent lamp assembly 577, supported on plate 579, is positioned by slots 565.

As illustrated in FIG. 1, head and chin rest assembly 19 includes a base support 581, two upright posts 583 and 585, chin rest bar 587 and brow rest 589. Base 581 is secured to a compound slide (not shown) for moving assembly 19 in the x, y and z directions. The x-direction movement is for left/right adjustment to center a patient's eyes with respect to refractor halves 71 and 73; y-direction movement, for in/out adjustment relative to refractor halves 71 and 73; and z-direction movement, for height adjustment. Chin rest bar 587 includes a U-shaped cutout 591 in which is received post 583. Bar 587 also includes a chin rest 593 and an elongated hollow boss 595 in which is slidably received post 585. A motor driven lead screw (not shown) received within post 585 carries a pin (not shown) which passes through a slot (also not shown) in post 585 and is coupled to the bar 587. Movement of the lead screw adjusts the relative position between bar 587 and brow rest 589.

In operation, instrument 11 is supported by an adjustable table. A patient whose eyes are to be examined is seated in front of instrument 11. Gross height adjustment is accomplished by raising or lowering the table. Additional gross adjustment, if necessary, may be accomplished by varying the height of the patient's chair. Once gross height adjustment is completed, final adjustment is accomplished by movement of the head and chin rest assembly 19. This may be accomplished in a number of different sequence adjustments of the compound slide which supports assembly 19, taken in conjunction with the tilt and interpupilary adjustments of refractor system 69. Once alignment is completed, instrument 11 is then normally shifted to the retinoscopy mode (FIGS. 16 and 17), then to the distance mode (FIGS. 2 and 3), and finally to the near vision testing mode (FIGS. 18 and 19).

The alignment mode of instrument 11 is schematically illustrated in FIG. 15. In this mode, shaft 57 of Brewster stereoscope 31 is rotated to move lenses 35 and 37 from optical paths 47 and 49; movable septum 273 of mask/septum system 61 is rotated, via drive shaft 283, from the position illustrated in FIG. 7 to, preferably, a position 90 degrees relative thereto; and shaft 293 of mode change system 63 is rotated to a position where neither optical path 47 nor 49 is folded. In this position, the instrument operator (identified by eyes 601 and 603) can, through window 299 provided in the rear of cover assembly 17, view the eyes (605 and 607) of the patient to be examined through the open apertures in refractor halves 71 and 73 to align refractor halves 71 and 73 with the eyes of the patient. Tilt adjustment of refractor halves 71 and 73, if necessary, is accomplished by rotation of one of knobs 211; inter-pupilary distance, by rotation of one of knobs 251.

With refractor halves 71 and 73 properly aligned relative to the patient's eyes, instrument 11 is normally changed to the retinoscopy mode, schematically illustrated in FIGS. 16 and 17. Shaft 57 of Brewster stereoscope 31 and shaft 293 of mode change system 63, are rotated to place lenses 35 and 37, folding mirrors 295 and 297, and fogging lenses 301 and 303 along optical paths 47 and 49. In this position, septum 273 of mask/septum system 61 does not separate optical paths 47 and 49. However, septum 313 of mask/septum system 65 is positioned between optical paths 47 and 49.

In the position illustrated in FIGS. 16 and 17, the opening between mirrors 295 and 297 is in alignment with window 299 to provide the instrument operator with a view of the patient's eyes through lenses 35 and 37 and the optics supported within refractor halves 71 and 73 to perform a retinoscopic examination with the same techniques utilized with conventional refractors such as illustrated in U.S. Pat. No. 3,860,330. As will be appreciated by those skilled in the art, for the purpose of retinoscopic examination, the patient's eyes should be focused at their far point. When this examination is done with a prior art refractor, this is accomplished by having the patient look through a 2D lens at a target placed approximately 6 meters away. A retinoscope is held approximately ½ meter from the patient's eyes. When the retinoscopic examination is performed using instrument 11, the retinoscope is positioned at window 299, also approximately ½ meter from the patient's eyes. However, because of the 3D power of lenses 35 and 37, a −1D retinoscopy lens (not shown) must be introduced into each of optical paths 47 and 49 to give a net power of +2D between the patient's eyes and the retinoscope. The retinoscopy lenses are carried by auxiliary disks 91 and 119. While producing the desired power between the patient's eyes and the retinoscope, the −1D retinoscopy lenses also changes the net power between the patient's eyes and the vision testing slide 41, which would induce accommodation by the patient with the result that the retinoscopic examination would be incorrect. In order to avoid this, fogging lenses 301 and 303, of positive power equal to or greater than the retinoscopy lens, are placed in optical paths 47 and 49 after mirrors 295 and 297 to relax the patient's accommodation.

Once the retinoscopic examination is complete, instrument 11 is normally shifted to the distance vision testing mode. Septum 273 of mask/septum system 61 is reinserted between optical paths 47 and 49 and shaft 293 of mode change system 63 is rotated to a position illustrated in FIGS. 2 and 3. Septum 313 of mask/septum system 65 remains in its position between optical paths 47 and 49. In this mode, patient views various vision testing slides supported on drums 341 and 343 of binocular target assembly 33. For masking selective portions of such targets, one or both of horizontal and vertical masks 333 and 331 of horizontal/vertical target mask system 67 are interposed in the optical path.

Once the patient's distance prescription is determined, lenses 35 and 37 of Brewster stereoscope 31 and septums 273 and 313 are removed from optical paths 47 and 49 to shift instrument 11 to the near vision testing mode illustrated in FIGS. 18 and 19. Removal of lenses 35 and 37 as well as removal of septums 273 and 313 is necessary so that the targets appear close to the patient and can be viewed directly and binocularly.

Though rotation of shaft 57 of Brewster stereoscope 31, shaft 283 of mask/septum system 61, shaft 293 of mode change system 63, shaft 323 of mask/septum system 65, and shafts 401 and 403 of target support system 33, could all be rotated manually, it is preferred that they be rotated automatically and in synchronization with each other so that the instrument operator can automatically change from one mode of operation to another. Preferably, this is accomplished by positively coupling shafts 57, 283, 293, 323, 401 and 403 to fine stepping motors and electronically generating control and drive signals to these stepping motors. The stepper pluse rate, number of pulses, direction control signals, selection of motor drives and position of each system is generated and monitored by a computer system. The computer system receives commands through an operator controlled keyboard or a positional encoder system, decodes these commands to generate the desired drive and position signals, and displays the system positions through an LED display. System position is obtained by monitoring one or more absolute optical position encoders on each system and also by translating the number of steps applied to each motor into a mechanical displacement for each system.

Whereas the drawings and the accompanying description have shown and described the preferred embodiment of the present invention, it should be apparent to those skilled in the art that various changes may be made in the form of the invention without affecting the scope thereof.

What I claim is:

1. A refraction instrument comprising:
   (a) housing means;
   (b) target means supported by said housing means, said target means including at least one binocular target having first and second halves;
   (c) first and second optical means, supported by said housing means, for making said target means appear at or near infinity when said target means is viewed through said optical means, said optical means and said target means defining a pair of optical paths;
   (d) first and second sets of corrective optics for emulating a series of ophthalmic prescriptions, said corrective optics supported relative to said housing means in optical alignment with said optical means;
   (e) means, supported by said housing means and interposed along said optical paths between said optical means and said target means, for separating said optical paths so as to provide separate and independent views of said halves of said binocular target;
   (f) means, supported by said housing means, for suppressing accommodation; and
   (g) apparatus, supported by said housing means between said optical means and said target means, for permitting retinoscopic examination through at least one of said first and second optical means and one of said sets of corrective optics while simultaneously maintaining a view of at least one of said halves of said binocular target through at least the other of said first and second optical means and other of said sets of corrective optics.

2. The refraction instrument as set forth in claim 1, wherein said means for separating said optical paths includes first and second septums, one of said septums positioned between said apparatus for permitting retinoscopic examination and said target means.

3. The refraction instrument as set forth in claim 2, wherein the other of said septums is positioned between said optical means and said apparatus for permitting retinoscopic examination.

4. The refraction instrument as set forth in claim 1 or 3, wherein said target means includes means for supporting a plurality of targets and alternately positioning one of said targets across said optical paths for viewing through said corrective optics and said optical means.

5. The refraction instrument as set forth in claim 4, wherein said means for supporting a plurality of targets includes a rotatable drum.

* * * * *